United States Patent
Hoffmann et al.

(10) Patent No.: US 8,146,441 B2
(45) Date of Patent: Apr. 3, 2012

(54) PROCEDURE FOR REGISTERING DAMAGE TO A MATERIAL

(75) Inventors: Daniel Hoffmann, Neukirchstockach (DE); Achim Schoberth, Taufkirchen (DE)

(73) Assignee: AIRBUS, Blagnac (FR)

( * ) Notice: Subject to any disclaimer, the term of this patent is extended or adjusted under 35 U.S.C. 154(b) by 270 days.

(21) Appl. No.: 12/669,648

(22) PCT Filed: Jul. 10, 2008

(86) PCT No.: PCT/EP2008/005652
§ 371 (c)(1),
(2), (4) Date: Jan. 19, 2010

(87) PCT Pub. No.: WO2009/010233
PCT Pub. Date: Jan. 22, 2009

(65) Prior Publication Data
US 2010/0192692 A1    Aug. 5, 2010

(30) Foreign Application Priority Data
Jul. 19, 2007 (DE) .......................... 10 2007 033 980

(51) Int. Cl.
*G01B 5/30* (2006.01)
(52) U.S. Cl. .......................................... 73/760; 73/800
(58) Field of Classification Search .................. 73/760, 73/800
See application file for complete search history.

(56) References Cited

U.S. PATENT DOCUMENTS

| | | | |
|---|---|---|---|
| 4,007,062 A | 2/1977 | Sifferlen | |
| 4,556,424 A | 12/1985 | Viswanadham | |
| 5,041,416 A * | 8/1991 | Wilson | ........................ 505/491 |
| 5,403,653 A * | 4/1995 | Moreton et al. | ........... 428/300.4 |
| 6,013,591 A | 1/2000 | Ying et al. | |
| 6,054,402 A | 4/2000 | Long et al. | |
| 6,361,888 B1 | 3/2002 | Kriven et al. | |
| 6,540,130 B1 | 4/2003 | Rödhammer | |
| 6,808,817 B2 * | 10/2004 | Morelli et al. | ................ 428/469 |
| 7,586,233 B2 * | 9/2009 | Schultz et al. | ................ 310/311 |

FOREIGN PATENT DOCUMENTS

| | | |
|---|---|---|
| AT | 001 239 U1 | 1/1997 |
| DE | 34 24 022 A1 | 1/1985 |
| WO | WO 90/05121 | 5/1990 |
| WO | WO 2005/005340 A1 | 1/2005 |

\* cited by examiner

*Primary Examiner* — Max Noori
(74) *Attorney, Agent, or Firm* — Oblon, Spivak, McClelland, Maier & Neustadt, L.L.P.

(57) ABSTRACT

A procedure for registering damage to a material including a metallic matrix and ceramic particles embedded in it. A volume-increasing phase change of the particles is suppressed by the pressure exerted on them by the metallic matrix. However, if a crack appears in the material, there is a phase change of the particles to a volume-increased phase which is detected by determining a measurement representing the proportion of the volume-increased phase.

9 Claims, 1 Drawing Sheet

PROCEDURE FOR REGISTERING DAMAGE TO A MATERIAL

Figure 1:
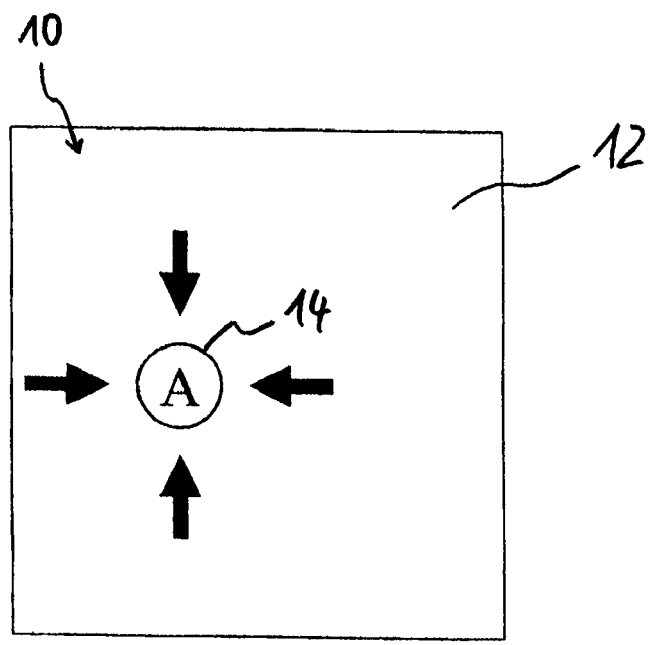

This invention concerns a procedure for registering damage to a material.

In particular, components that are subjected to lesser or greater mechanical stresses during use often suffer from the problem of gradual fissure formation in the material concerned. In practice, the moment at which damage to the material starts to occur is hard to predict.

For this reason technical equipment or its individual components are subjected to a considered inspection on a rotational basis. An example of this is the aircraft industry. In this sphere, components whose function is critical for safety are often replaced as a precaution even if this is not essential.

DE 34 24 022 C2 cites the manufacture of a composite body, usable as a material, from an essentially vitreous metal as a matrix alloy and at least one kind of secondary-phase particles, dispersed evenly throughout the matrix alloy. A cobalt, nickel or iron-based alloy is chosen preferentially as the matrix alloy. Carbon, nitride, oxide, boride, silicate and metal are cited as examples of secondary-phase particles. In particular, the material described should be a highly wear-resistant magnetic material, potentially suitable for the production of magnetic heads.

U.S. Pat. No. 4,007,062 cites a material consisting of an aluminium matrix with embedded ceramic particles. Various procedures for manufacturing the material are also described in this publication.

AT 001 239 U1 cites a procedure for the manufacture of a composite material comprising matrix components consisting of one or more metals and a stiffening component. While the material is being made, these components are bound indissolubly together by the effect of pressure and/or temperature. One or more compounds are considered as a stiffening component, chosen from the group of carbides, borides, nitrides and oxides of the metals of group IVB-VIB, silicon, boron, aluminium and rare-earths.

It is the task of the present invention to enable the necessary repair or maintenance of parts that are subject during use to the formation of fissures which are hard to assess.

According to the invention this task is performed by a method that records damage to materials as per Claim 1. The dependent claims involve advantageous extensions of the invention.

In what follows attention is first given to materials and processes for their manufacture, suitable for implementation of the invention, and there is then a detailed description of the material-damage registration procedure according to the invention.

The material intended for implementation of the invention comprises a metallic matrix with embedded ceramic particles, whereby a volume-increasing phase alteration of the particles is suppressed by pressure exerted on the particles by the metallic matrix.

In a component made of such a material it is comparatively easy to determine by means of the procedure according to the present invention where and how mechanical damage has occurred. In case of incipient fissuring, the pressure exerted by the metallic matrix declines more or less abruptly on those particles which are near a fissured surface or adjacent to such a surface. This pressure reduction around a fissure in the material initiates the previously suppressed phase change, so that cracks can be identified promptly by detecting phase-changed particles with an enlarged volume. This in turn enables the necessary repair or maintenance activity for the component concerned.

In a further development of the material to support the invention, the substance of the particles is selected so that, in case of fissuring around the particles, the recognized 'crack closure' or 'particle reinforcement' effect results ('transformation toughening').

It is the intention that the matrix should be a steel as an embodiment of this concept.

Another embodiment of this concept involves selecting a light metal alloy, especially an aluminium alloy, for this purpose.

Such matrix materials are especially suitable, for example, for the manufacture of structural parts for vehicles, especially aircraft. For example, recognized aluminium alloys with "7xxx" or even "6xxx" classification can be employed as a matrix material to good advantage.

A component to be investigated by using the procedure according to the invention does not have to be composed entirely of the material described above. Rather, it is also possible to envisage this material as an element of a composite, for example as the surface coating of a component.

Recourse can also be had to known ceramic materials when the material for the ceramic particles is being selected. For example, this may involve particles consisting of zirconium dioxide, in which the volume-increasing phase change from the tetragonal to the monoclinic phase is suppressed.

This is mentioned of course by way of example only. In practice, other ceramic materials and other phase changes, preferably transformations of the crystal structure of the ceramic concerned between two different crystal systems, may be envisaged.

In summary, the basic notion for the material to be investigated by the invention involves integration of special particles in the material that alter an easily detectable property (phase) if mechanical damage such as crack in the vicinity of such particles occurs. To some extent the particles act as 'integrated detectors' that respond to a drop in mechanical pressure around the fissure.

A transformation of the crystallographic structure of the particles is particularly easily recorded, so that any damage to the material can be promptly highlighted.

An appropriate procedure for producing a material suited to the invention encompasses the following steps:
  Introduction of ceramic particles into a metallic matrix at a raised temperature at which the particles present a comparatively small volume, and
  Cooling of the metallic matrix with the embedded ceramic particles so that a volume-increasing phase change of the particles is impeded by the pressure exerted on the particles by the matrix.

In this way, materials can be produced quite easily. The special forms of procedure and types of materials described above can be made analogously by correspondingly special process features.

One form of the manufacturing procedure involves introducing the particles into the matrix at a temperature that is close to the melting point of the matrix or even higher than its melting point.

A particularly advantageous form of production involves introducing the particles into the matrix during an extrusion process. In this way, for example, aluminium sections can be produced in a way that accords with the invention. Alternatively, an HIP process followed by an extrusion process can be used, or indeed another suitable consolidation process.

Before and/or during cooling of the metallic matrix with its embedded ceramic particles, the material can be generally shaped or moulded to good effect, for example, by creating the desired final profile of a component or semi-finished part.

By means of the production process described parts or components (e.g. for composite parts) or indeed semi-finished items, such as plates or sections, can be made.

The procedure, according to the invention, for registering damage to a material of the type described above or to a material that has been produced by the procedure described here involves determining a size, in particular a physical measurement, that represents the proportion of the volume-increased phase of the particles in the material.

For such damage registration radiation- or wave-based methods are particularly interesting, as such phenomena pass through the matrix material in a more or less unhindered fashion but interact preferentially with the embedded particles. In case of a comparatively small penetration depth of the radiation or waves used, there is nonetheless the possibility of demonstrating material damage in areas near the surface of the component or material concerned.

The measurement can be determined, for example, by using sound waves, especially ultrasound waves. In another form of the procedure the measurement can be determined by using electromagnetic radiation, for example X-rays or terahertz radiation.

In the event that the phase change of the particles is a crystallographic phase change, it is particularly advantageous if the wave length of the radiation used (e.g., also neutron radiation, etc.) is of the same order of magnitude as the typical lattice spacing of the crystallographic structures involved. In that case, determination of size may depend on interference effects or measurement accuracy may be improved by such effects. An example of such an interference-based measurement method is X-ray diffraction ('XRD') which can be employed advantageously in the context of the invention. Naturally, the use of diffraction effects in the context of registering damage according to the invention is in no way restricted to electromagnetic radiation, particularly X-rays. In fact other recognized forms of radiation can be deployed to good effect in this respect.

One preferred form of the procedure involves determination of the measurement in terms of spatial resolution. In this way not only damage to the material can be effectively detected as such but information on its spatial distribution or on the location of individual areas of damage can be obtained.

One form of the procedure involves the measurement being representative of the volumetric proportion of the volume-increased phase (e.g. absolute or relative volume with respect, for example, to the total volume of the material being investigated).

Alternatively or additionally it is particularly advantageous if the measurement is representative of the proportion of the volume-increased phase with respect to the proportion of the volume-reduced phase. If, in fact, such a comparative measurement between the proportions of the particles in their initial condition and their transformed condition is made, no external reference for comparison or measurement calibration is required. Indeed, to a large extent determination of a measurement based on an internal reference within the material is possible with great accuracy without a prior comparative measurement or calibration. Furthermore, a proportion measured in this way is relatively stable to fluctuations in the initial particle concentration within the material and in the measurement conditions.

Hence, by registering damage according to the invention a quantitative and also a potentially localized evaluation of material damage is possible. In particular, the procedure can be very valuable for a structural component of a technical installation made from the material, for example for better planning of rotational inspections or for replacement by necessity-based inspections (e.g. targeted necessity-based repairs to parts).

The invention is further described below, based on an example of the procedure with reference to the attached drawings. These show:

FIG. 1 a schematic representation of a material in an initial condition, and

Figure 2:
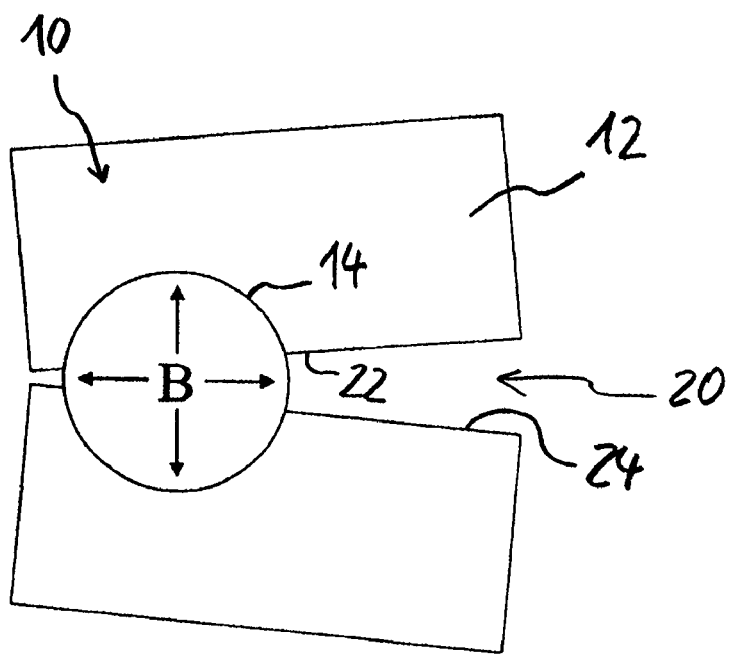

FIG. 2 a representation as per FIG. 1 with the formation of a fissure in the material.

FIG. 1 illustrates a material 10, encompassing a metallic matrix 12 and ceramic particles embedded in it, of which, for the sake of clarity, only one is depicted and denoted 14.

In fact, many particles (14) are finely distributed throughout the metallic matrix 12 (e.g. an aluminium alloy).

According to the method for manufacturing the material 10, the particles 14 are present in the matrix 12 in a particular (here: crystallographic) phase, designated in the figure by an 'A'.

The arrows in FIG. 1 symbolize the mechanical pressure which is exerted by the material of the matrix 12 on the particles 14 and stabilizes phase A. At the temperature at which the material 10 or a component made of it is used, the particles 14 would normally undergo a volume-increasing phase change. This phase change, however, is suppressed by the mechanical pressure exerted on the particles 14.

If the material has now been used for a certain time and been subjected to corresponding stresses, there is a danger that fissuring may occur at any time in the material 10.

FIG. 2 illustrates the material in a condition damaged by such fissuring. The figure depicts a crack 20 running through the material 10 and bordered by crack surfaces 22 and 24 accordingly.

If this crack 20, as depicted, encounters the particle 14 or such a particle 14 is located in the immediate vicinity of one of the crack edges 22 and 24, the previously inhibited phase change of particle 14 is triggered by the pressure reduction around the crack 20. Hence all particles 14 located around the crack 20, such as the particle 14 depicted, are transformed to a volume-increased phase, as symbolized in FIG. 2 by arrows, with the phase marked with a 'B'.

The damage to the material 10 by the crack 20, as depicted in FIG. 2, can also be registered by a suitable physical measurement procedure, whereby a magnitude representing the proportion of the volume-increased phase B of the particle 14 in the material 10 is determined. The measurement method could be X-ray diffraction, for example glancing-angle X-ray diffraction ('GAXRD'). Alternatively or additionally, terahertz radiation can also be used, for example, to detect the presence of phase B, and this can be easily generated, for example, by difference frequency mixing from lasers with wavelengths in the infrared region.

The more that the material 10 is damaged by fissures, the greater the proportion of phase B compared with the proportion of phase A in the material becomes. Hence, when damage to the material is registered, a phase ratio (proportion of phase B/proportion of phase A) can be determined as a useful measurement to obtain a quantitative scale for the damage.

As an absolute or relative proportion of phase B only changes spatially where material damage is actually in evidence, spatially-resolved registration of fissures in the material 10 can also be effected by making a measurement of space resolution.

In practice, such a procedure for registering damage to material can be very useful, for example, for a structural component made from the material 10 in the aerospace industry, in order to register material damage at various depths, in a contact-free fashion, for example by X-ray diffraction.

The invention claimed is:

1. A procedure for registering damage to a material including a metallic matrix with ceramic particles embedded in it, comprising:
    suppressing a volume-increasing phase change of the particles by pressure exerted on the particles by the metallic matrix; and
    making a measurement representing the proportion of the volume-increased phase of the particles in the material.

2. A procedure according to claim 1, in which the measurement is made by electromagnetic radiation.

3. A procedure according to claim 1, in which the measurement is made by spatial resolution.

4. A procedure according to claim 1, in which the measurement is representative of a volumetric proportion of the volume-increased phase.

5. A procedure according to claim 1, in which the measurement is representative of the proportion of the volume-increased phase relative to the proportion of the volume-reduced phase.

6. A procedure according to claim 1, carried out on a structural component of a technical installation made of the material.

7. A procedure according to claim 1, carried out on a material whose matrix is a steel.

8. A procedure according to claim 1, carried out on a material whose matrix is a light-metal alloy, or an aluminium alloy.

9. A procedure according to claim 1, carried out on a material whose particles are formed from zirconium dioxide, in which the volume-increasing phase change from a tetragonal phase to a monoclinic phase is inhibited.

* * * * *